(12) United States Patent
Maison et al.

(10) Patent No.: US 8,829,233 B2
(45) Date of Patent: Sep. 9, 2014

(54) TRIPODAL BISPHOSPHONATE DERIVATIVES

(75) Inventors: Wolfgang Maison, Winsen (DE); Elisa Franzmann, Wettenberg-Wißmar (DE); Faiza Khalil, Mucke (DE)

(73) Assignee: Justus-Liebig-Universitaet Giessen, Giessen (DE)

( * ) Notice: Subject to any disclaimer, the term of this patent is extended or adjusted under 35 U.S.C. 154(b) by 0 days.

(21) Appl. No.: 13/821,321

(22) PCT Filed: Sep. 7, 2011

(86) PCT No.: PCT/EP2011/065495
§ 371 (c)(1),
(2), (4) Date: Jun. 4, 2013

(87) PCT Pub. No.: WO2012/032093
PCT Pub. Date: Mar. 15, 2012

(65) Prior Publication Data
US 2013/0267731 A1     Oct. 10, 2013

(30) Foreign Application Priority Data
Sep. 10, 2010 (EP) ..................... 10176296

(51) Int. Cl.
*C07F 9/22* (2006.01)
*C07F 9/38* (2006.01)
(52) U.S. Cl.
CPC ..................... *C07F 9/3873* (2013.01)
USPC .............................. 562/15; 562/20
(58) Field of Classification Search
None
See application file for complete search history.

(56) References Cited

PUBLICATIONS

Houpert et al.,Human & Experimental Toxicology (2001) 20, 237-241.*
Database Caplus Chemical Abstracts Service, Columbus, Ohio, US; Database Accession No. 2001:818365, Abstract of Lecouvey et al., Tetrahedron Letters (2001), 42(48), 8475-8478.*
J. Young, et al., ""Smart" Cascade Polymers. Modular Syntheses of Four-Directional Dendritic Macromolecules with Acidic, Neutral, or Basic Terminal Groups and the Effect of pH Changes on Their Hydrodynamic Radii", *Macromolecules*, 27:3464-71(1994).
R. Burgada, et al., "Synthesis of Bisphosphonic Ligands for the Complexation of the Uranyl Ion, Cobalt and Iron", *C.R. Chimie*, 7:35-39 (2004).
Burgada, et al., "Synthetic Strategy of New Powerful Trisbisphosphonic Ligands for Chelation of Uranyl, Iron, and Cobalt Cations", *Tetrahedron Letters*, 48:2315-19 (2007).
S. Zhang, et al., "'Magic Bullets' for Bone Diseases: Progress in Rational Design of Bone-seeking Medicinal Agents", *Chem. Soc. Rev.*, 36:507-31 (2007).

K. Yoon, et al., "Monofunctionalization of Dendrimers with Use of Microwave-Assisted 1,3-Dipolar Cycloadditions", *Organic Letters*, 9(11):2051-54 (2007).
M. Sawicki, et al., "Bisphosphonate Sequestering Agents. Synthesis and Preliminary Evaluation for in vitro and in vivo Uranium(VI) Chelation", *European Journal of Medicinal Chemistry*, 43:2768-27 (2008).
R. Ehrick, et al., "Ligand-Modified Aminobisphosphonate for Linking Proteins to Hydroxyapatite and Bone Surface", *Bioconjugate Chem.*, 19(1):315-21 (2008).
J. Wach, et al., "Antimicrobial Surfaces Through Natural Product Hybrids", *Angew. Chem. Int Ed.*, 47:7123-26 (2008).
M. Kleinert, et al., "A Modular Approach for the Construction and Modification of Glyco-SAMs Utilizing 1,3-dipolar Cycloaddition",*Org. Biomol. Chem.*, 6:2118-32 (2008).
G. Franc, et al., "gem-Bisphosphonate-Ended Group Dendrimers: Design and Gadolinium Complexing Properties",*Eur. J. Org. Chem.*, 25:4290-99 (2009).
M. Wyszogrodzka, et al., "Study of Single Protein Adsorption onto Monoamino Oligoglycerol Derivatives: A Structure-Activity Relationship", *Langmuir*, 25(10):5703-12 (2009).
International Search Report in International Application No. PCT/EP2011/065495 issued/mailed on Nov. 2, 2011, 4 pages.

\* cited by examiner

*Primary Examiner* — Karl J Puttlitz
(74) *Attorney, Agent, or Firm* — Marshall, Gerstein & Borun LLP

(57) ABSTRACT

The present invention describes tripodal bisphosphonate derivatives with a flexible basic framework for the functionalization of surfaces, and methods for their production and use. The central atom of the flexible framework is hereby a tertiary aliphatic carbon atom. A fourth remaining position of the flexible framework is suitable to be optionally functionalized by so-called click reactions, for example with biomolecules, polyethylene glycol or active agents.
The compounds according to the present invention have the general formula X—C{(CH$_2$)$_n$—Y—C[PO(OH)$_2$]$_2$R$^1$}$_3$, wherein X stands for a group —(CH$_2$)$_p$—R$^3$, wherein p=0 to 10 and R$^3$ is selected from —H, —NH$_2$, —NO$_2$, —OH, —SH, —O—NH$_2$, —NH—NH$_2$, —N=C=S—, —N=C=O—, —CH=CH$_2$, —C≡CH, —COOH, —(C=O)H, —(C=O)R$^4$ Y stands for —CH$_2$—, —CH=CH—, —C≡C—, —O—, —S—, —S—S—, —NH—, —O—NH—, —NH—O—, —HC=N—O—, —O—N=CH—, —NR$^2$—, -aryl-, -heteroaryl-, —(C=O)—, —O—(C=O)—, —(C=O)—O—, —NH—(C=O)—, —(C=O)—NH—, —NR$^2$—(C=O)—, —(C=O)—NR$^2$—, —NH—(C=O)—NH—, —NH—(C=S)—NH—, R$^1$ represents a hydrogen atom or a hydroxy group, R$^2$ stands for a linear or branched alkyl group and R$^4$ for a linear or branched alkyl group or an aryl group. The production of the compounds occurs by reacting a compound X—C[(CH$_2$)$_n$—Y']$_3$ with a reagent Y"C[PO(OH)$_2$]$_2$R$^1$ to the corresponding compound X—C{(CH$_2$)$_n$—Y—C[PO(OH)$_2$]$_2$ R$^1$}$_3$ and subsequent purification of the reaction product. Y' and Y" are hereby precursors of Y. The compounds according to formula (I) according to the present invention are suitable to be used in a method to functionalize surfaces. The X group of the compounds according to the present invention is suitable to be optionally coupled to an effector, for example, by means of click chemistry.

6 Claims, No Drawings

TRIPODAL BISPHOSPHONATE DERIVATIVES

BACKGROUND OF THE INVENTION

1. Field of the Invention

The present invention relates to the fields of organic chemistry and material sciences.

2. Brief Description of Related Technology

The state of the art recognises numerous methods for the functionalisation of surfaces. Such functionalisations are used in order to modify the material properties of the surfaces in a targeted manner. Such functionalisations should be as durable as possible and allow for a highly defined loading of the surface.

In the field of medical technology, special importance is placed on functionalised surfaces. Implants should—by way of example in the dental industry and orthopedics (joint replacement)—be as biocompatible as possible, i.e. by not have, inter alia, having a tendency towards biofouling, not causing any inflammatory reactions and not being seeded with pathogenic microorganisms. Furthermore, they must permanently resist to heavy mechanical strain.

Bisphosphonates belong to a group of pharmaceuticals which has been developed during the last 30 years for diagnostic and therapeutic purposes with regard to bone and calcium metabolic diseases. Some compounds of this type are used in pharmaceuticals for the treatment of osteoporosis. The are approved in Germany for the therapy of osteoporosis in postmenopausal women, osteodystrophia deformans and the hypercalcemia associated with tumors. Furthermore, they are used in the treatment of bone metastases and fibrous dysplasia.

Ongoing research with the aim to find bone specific therapeutics based on bisphosphonates is described in S Zhang, G Gangal, H Uludag: 'Magic bullets' for bone diseases: progress in rational design of bone-seeking medicinal agents", Chem Soc Rev 2007, 36, 507-531. In R S Ehrick, M Capaccio, D A Puleo, L G Bachas: "Ligand-Modified Aminobisphosphonate for Linking Proteins to Hydroxyapatite and Bone Surface", Bioconjugate Chem 2008, 19, 315-321, a synthesis route to bind tetraethyl(aminomethylene)bisphosphonate (AMB) to biotin, and the binding of AMB biotin to hydroxylapatite.

Methods suitable to coat antimicrobially surfaces with natural product hybrids are described in J-Y Wach, S Bonazzi, K Gademann: "Antimikrobielle Oberflächen durch Naturstoffhybride" (Antimicrobial surfaces due to natural product hybrids), 120, 7232-7235. The natural product hybrids comprise monomeric catecholamines.

Examinations with regard to structure-activity relationships of methylated or hydroxyterminated polyglycerol structures, which were deposited as SAMs on surfaces of gold, are described in M Wyszogrodzka, R Haag: "Study of Single Protein Adsorption onto Monoamino Oligoglycerol Derivatives: A Structure-Activity Relationship", Langmuir 2009, 25, 5703-5712. The dendritic polyglycerol structures shown do not comprise any bisphosphonates.

In J K Young, G R Baker, G R Newkome: "Smart Cascade Polymers. Modular Syntheses of Four-Directional Dendritic Macromolecules with Acidic, Neutral, or Basic Terminal Groups and the Effect of ph Changeson their Hydrodynamic Radii", Macromolecules 1994, 27, 3464-3471 are described examples for the synthesis of fourdirectional, flexible and dentritic cascade polymers. The disclosed dendritic molecules, however, do not comprise any bisphosphonate groups.

In K Yoon, P Goyal, M Weck: "Monofunctionalization of Dendrimers with Use of Microwave-Assisted 1,3-Dipolar Cycloadditions", Org Lett 2007, 9, 2051-2054, are also described methods for the production of flexible dendritic compounds. The work discloses, inter alia, the introduction of cyclic functional groups via 1,3-dipolar cycloadditions. M Kleinert, T Winkler, A Terfort and T B Lindhorst describe in "A modular approach for the construction and modification of glyco-SAMs utilizing 1,3-dipolar cycloaddition", Org Biomol Chem 2008, 6, 2118-2132 also methods for the modular synthesis of flexible dendritic compounds. In addition to 1,3 dipolar cycloadditions are also described click reactions on SAMs.

Until now, the state of the art does not know a way of bonding bisphosphonates to trivalent flexible skeletons.

SUMMARY OF THE INVENTION

For the first time, the present invention provides trivalent flexible skeletons with ligands comprising bisphosphonate units. The compounds according to the present invention comprise tripodal flexible skeletons with one tertiary aliphatic carbon atom to which three bisphosphonate units are bonded. The remaining fourth substituent of the tertiary carbon atom is easily suitable to be further functionalised via so-called click reactions, e.g. with biomolecules, dyes, radiomarkers, polyethylene glycol or active agents.

DETAILED DESCRIPTION

The aim of the present invention is to provide compounds which allow for a durable functionalisation and a highly defined loading of surfaces, and methods for the production of these compounds.

The present invention describes tripodal bisphosphonate derivatives with a flexible basic framework for the functionalisation of surfaces, and methods for their production and use. The central atom of the flexible framework is hereby a tertiary aliphatic carbon atom. A fourth remaining position of the flexible framework is suitable to be optionally functionalised by so-called click reactions, for example with biomolecules, polyethylene glycol or active agents.

The task, namely to provide compounds which allow for a durable functionalisation and a highly defined loading of surfaces is achieved according to the present invention via compounds according to formula (I):

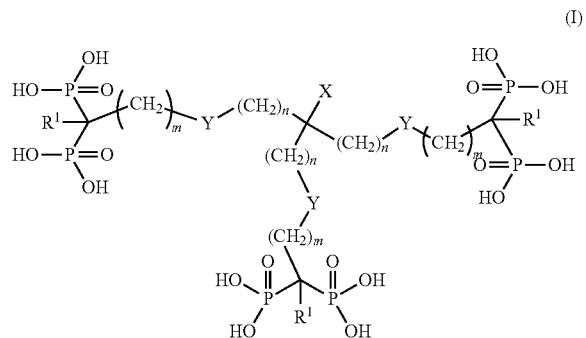

wherein n and m stand independently of one another for integers between 0 and 10, $R^1$ is a hydrogen atom or a hydroxy group, Y is selected from —$CH_2$—, —CH=CH—, —C≡C—, —O—, —S—, —S—S—, —NH—, —O—NH—, —NH—O—, —HC=N—O—, —O—N=CH—, —$NR^2$—, -aryl-, -heteroaryl-, —(C=O)—, —O—(C=O)—, —(C=O)—O—, —NH—(C=O)—, —(C=O)—NH—, —$NR^2$—(C=O)—, —(C=O)—$NR^2$—, —NH—(C=O)—NH—, —NH—(C=S)—NH—, wherein $R^2$ stands for a linear alkyl group with 1 to 10 C atoms or a branched or cyclic alkyl group with 3 to 10 C atoms, and X stands for a group —$(CH_2)_p$—$R^3$, wherein p=0 to 10 and $R^3$ is selected from —H, —$NH_2$, —$NO_2$, —OH, —SH, —O—$NH_2$, —NH—$NH_2$, —N=C=S—, —N=C=O—, —CH=$CH_2$, —C≡CH, —COOH, —(C=O)H, —(C=O)$R^4$, wherein the hydroxy, thio, amino or C=O groups are optionally suitable to be protected by a protective group, —$N_3$, —$OR^4$, —$COOR^4$, —$NHR^4$, —$NR^4R^5$, —CO—$NHR^4$, —$CONR^4R^5$, —NH—CO—$R^4$, 4-(2,5-dioxopyrrol-1-yl), wherein $R^4$ and $R^5$ stand independently of one another for a linear alkyl group with 1 to 10 C atoms, a linear alkenyl or alkynyl group with 2 to 10 C atoms, a branched alkyl, alkenyl or alkynyl group with 3 to 10 C atoms or a cyclic alkyl or alkenyl group with 3 to 10 C atoms, or X stands for a branched alkyl, alkenyl or alkynyl group with 3 to 10 C atoms or a cyclic alkyl, alkenyl or alkynyl group with 3 to 10 C atoms or for an aryl or heteroaryl group, wherein, in the event that X is a branched alkyl, alkenyl and alkynyl group, a cyclic alkyl or alkenyl group, an aryl or heteroaryl group, one C atom of this group X is optionally suitable to carry one group $R^3$ according to the definition above.

The compounds according to the present invention, the method for their production and the use of these compounds are explained hereinafter.

The invention is not limited to one of the embodiments described hereinafter; rather, it is suitable to be modified in various different ways.

All of the characteristics and advantages originating from the claims, description and figures (including constructive details, spatial arrangements and processing steps) are suitable to be essential to the invention, both in themselves and in the most various combinations.

The compounds according to formula (I) according to the present invention allow for a durable functionalisation and a highly defined loading of surfaces. Surfaces which are suitable to be functionalised and loaded comprise metals, metal oxides, apatite, glass and mixtures thereof. The term "apatite" hereby comprises both compounds following the general formula $Ca_5(PO_4)_3(F,Cl,OH)$, in which the concentration of fluoride, chloride and hydroxyl ions is freely exchangeable, and the single minerals fluoroapatite, chloroapatite and hydroxylapatite.

Under "highly defined loading" is understood that the loading of the surface allows for a gap-free coating of the material in the form of a monolayer. "Monolayer" is understood to mean a layer of molecules according to the present invention on the surface which has a height of just a single molecule. A "functionalisation" is the addition of functional groups to the surface of a material via chemical synthesis methods. A coating of surfaces with the compounds according to the present invention thus represents a functionalisation of these surfaces. An effector molecule is optionally suitable to be bonded to the group X. This represents another functionalisation. An effector is a molecule or a molecule component which causes a physical, chemical, biochemical or biological process or controls, activates or inactivates such an effect. Examples for effectors are dyes, radioactive molecules, biomolecules such as amino acids, sugar, peptides, proteins, DNA, RNA, polymers such as ethylene glycol and derivatives thereof as well as active agents. Substances are referred to as active agents if they cause a specific effect or a reaction in low doses within an organism.

Due to the multivalent binding of the compounds according to formula (I), this functionalisation is durable in comparison to molecular exchange processes on the surface (such as the hydrolysis of the coupling in aqueous media) and also in comparison to mechanical strain.

It is known to persons skilled in the art that cyclic alkyl and alkenyl groups have to comprise at least three carbon atoms. In the context of the present invention, "annular" groups are understood to mean such groups in which all carbon atoms are involved in the ring formation. Furthermore, "cyclic" groups are suitable to also comprise acyclic carbon atoms. In the context of the present invention, annular alkyl and alkenyl groups are propyl, butyl, pentyl, hexyl, heptyl, octyl, nonyl, decyl, propenyl, butenyl, pentenyl, hexenyl, heptenyl, octenyl, nonenyl and decenyl rings. If the groups X, $R^4$ and/or $R^5$ are cyclic alkyl or alkenyl groups, they are selected from the aforementioned annular alkyl and alkenyl groups which do not carry further substituents, and from the aforementioned annular alkyl and alkenyl groups which are themselves bonded to one or several acyclic alkyl, alkenyl or alkynyl groups. In the latter case, the binding of the cyclic alkyl or alkenyl group to the C1 atom of the adamantane skeleton (provided that the cyclic group represents X) or to the respective atom of the group $R^5$ (provided that the cyclic group represents $R^4$ or $R^5$) is suitable to occur via a cyclic or acyclic carbon atom of the cyclic alkyl or alkylene group. According to the above definition of the term "alkyl group", cyclic alkyl groups also comprise a total of 10 carbon atoms maximum.

According to the present invention, the group X is a group —$(CH_2)_p$—$R^3$. If $R^3$ is —$NH_2$, —OH, —SH, —O—$NH_2$, —NH—NH—COOH, —(C=O)H, —(C=O)$R^4$, these groups are optionally suitable to be protected by a protective group. Protective groups for hydroxy, thiol, amino, carbonyl and carboxyl groups are known by persons skilled in the art. They are able to use these protective groups, i.e. to introduce and, if required, cleave them off again, without leaving the scope of protection of the patent claims.

By way of non-exhaustive example the following protective groups are to be named:

for the OH group: methoxy methyl ether (MOM), β-methoxy ethoxy methyl ether (MEM), silyl ether, 2-tetrahydropyranyl (THP), acetyl (Ac), benzoyl (Bz), benzyl (Bn, Bnl), dimethoxytrityl (DMT), methoxytrityl (MMT), p-methoxy benzyl ether (PMB), methylthiomethyl ether, pivaloyl (piv), methylether, ethoxyethyl ether (EE)

for the SH group: tert-butyl, 2-tetrahydropyranyl, acetyl, 2-nitropyranyl, phenacyl, (cumarin-4-yl)methyl for the $NH_2$ group: 1-(1-adamantyl)-1-methoxycarbonyl (ADPOC), allyl-oxycarbonyl (ALLOC), benzyloxycarbonyl (abbreviated by Z or Cbz), 9-fluorenylmethoxycarbonyl (FMOC), p-methoxybenzyl carbonyl (Moz, MeOZ), tert-butyloxycarbonyl (BOC), acetyl (ac), benzoyl (Bz), benzyl (Bn, Bnl), p-methoxybenzyl (PMB), 3,4-dimethoxybenzyl (DMPM), p-methoxyphenyl (PMP), Tosyl (ts), sulfonamides for the carbonyl group (in aldehydes and ketones): the reaction with diols to acetals or ketals for the COOH group: methylester, benzyl ester, tert-butyl ester, silyl ester, orthoester, oxazolines According to the present invention, aryl groups are understood to mean phenyl, naphthyl and anthracenyl groups.

Heteroaryl groups are selected from furanyl, pyrrolyl, thiophenyl, imidazolyl, pyrazolyl, triazolyl, thiazolyl, oxazolyl, isooxazolyl, one oxadiazolyl, pyridinyl, pyrazinyl, pyrimidinyl, pyridazinyl, one triazinyl, one tetrazinyl, 1,4-dioxinyl, one thiazinyl, one oxazinyl, one azepinyl, a diazepinyl, benzofuranyl, isobenzofuranyl, indolyl, isoindolyl, benzothiophenyl, benzo[c]thiophenyl, benzimidazolyl, purinyl, indazolyl, benzoxazolyl, benzisoxazolyl, benzothiazolyl, quinolinyl, isochinolinyl, chinoxalinyl, acridinyl, chinazolinyl and cinnolinyl.

In an advantageous embodiment, Y is selected from no atom, —$CH_2$—, —NH—(C=O)—, —(C=O)—NH—, —$NR^2$—, wherein $R^2$ is as defined above.

In another advantageous embodiment, n is an integer between 0 and 3.

In another advantageous embodiment, m is an integer between 0 and 3.

Particularly advantageously, n and m stand independently of one another for integers between 0 and 3.

In a further advantageous embodiment, X represents a group (—$CH_2$)$_p$—$R^3$, wherein p represents an integer between 0 and 3 and $R^3$ is defined as in claim 1.

In another advantageous embodiment, X stands for —$(CH_2)_p$—$R^3$, wherein $R^3$ is selected from —H, —OH, —$NH_2$, —$NO_2$, —NH—$NH_2$, —$NHR^4$, —$NR^4R^5$, —O—$NH_2$, —NH—(C=O)—C≡CH, —C≡CH, —N=C=S, —N=C=O, —COOH, —(C=O)H, —(C=O)$R^4$, and wherein p represents an integer between 0 and 3, and $R^4$ and $R^5$ are defined as above.

The compounds according to formula (I) are produced by reacting a compound X—C[$(CH_2)_n$—Y']$_3$ with a reagent Y"C[PO(OH)$_2$]$_2R^1$ to the corresponding compound X—C{$(CH_2)_n$—Y—C[PO(OH)$_2$]$_2R^1$}$_3$ and by subsequent purification of the reaction product, wherein Y' stands for a precursor of the group Y according to formula (I) and wherein X, $R^1$ and n are defined as in formula (I).

Precursor is hereby understood to refer to a functional group which is converted via reaction with another functional group acting as precursor or a further reagent acting as precursor into a functional group according to formula (I).

Compounds of the formula X—C[$(CH_2)_n$—Y']$_3$ are known. Persons skilled in the art are able to commercially purchase them or produce them independently with the help of their specialist knowledge following known synthesis procedures.

In an advantageous embodiment, X is a hydrogen atom.

In another advantageous embodiment, X is a group —$(CH_2)_p$—$R^5$, wherein p represents an integer between 0 and 3, and $R^5$ is selected from —OH, —$NH_2$, —$NO_2$, —NH—$NH_2$, —$NHR^6$, —$NR^6R^7$, —O—$NH_2$, —NH—(C=O)—C≡CH, —C≡CH, —N=C=S, —N=C=O, —COOH, —(C=O)H, —(C=O)$R^6$, wherein $R^6$ and $R^7$ are defined as in formula (I). As already indicated, these groups may be optionally protected via a protective group (Pg). If these groups are protected, this occurs before the reaction with the reagent Y"Z, so that in this case Pg-X—C[$(CH_2)_n$—Y']$_3$ is reacted with a reagent Y"C[PO(OH)$_2$]$_2R^1$ to the corresponding compound Pg-X—C{$(CH_2)_n$—Y—C[PO(OH)$_2$]$_2R^1$}$_3$.

Suitable protective groups are described above. It is known to persons skilled in the art how to introduce these protective group and remove them again. Persons skilled in the art are able to apply this knowledge without leaving the scope of protection of the patent claims.

The purification of the reaction product occurs, by way of example by removing the solvent, adding the residue to a mixture comprising a polar aprotic solvent such as ethyl acetate and a diluted mineral acid, e.g. diluted hydrochloric acid, washing with a saturated $KHSO_4$ solution and drying.

In an advantageous embodiment, Y"C[PO(OH)$_2$]$_2R^1$ is an amino or alcohol functionalised bisphosphonate, such as pamidronate or alendronate and their protected derivatives. In this case, X—C[$(CH_2)_n$—Y']$_3$ or Pg-X—C[$(CH_2)_n$—Y']$_3$ is reacted with Y"C[PO(OH)$_2$]$_2R^1$ in the presence of an activating reagent and a coupling additive if required. Y' is hereby a carboxylic acid residue or a derivative thereof. Suitable activating reagents are, by way of example, EDC, DCC, DCI, PyClop, HBTU, HATU, HOSu, TBTU, T3P, BopCl and 3-Cl-1-pyridinium iodide. The substances HOBT, HOAt, HONB and NHS known to persons skilled in the art are usable, by way of example, as coupling additives. It is known to persons skilled in the art that these reactions are appropriately carried out with the addition of a base such as DIPEA. Persons skilled in the art are furthermore aware of different solvents to be used in the methods mentioned. They are able to independently produce these combinations of activating reagents, coupling additives, bases and solvents using their conventional knowledge and standard literature.

If a protective group Pg has been introduced and/or protected bisphosphonates have been used, these protective groups are removed at the end, and the deprotected product is subsequently purified. In another advantageous embodiment, Y"C[PO(OH)$_2$]$_2R^1$ is an carboxyl functionalised bisphosphonate, such as dicarboxypropane-1,1-diphosphonate (DPD) or one of its protected derivatives. In this case, X—C[$(CH_2)_n$—Y']$_3$ or Pg-X—C[$(CH_2)_n$—Y']$_3$ is reacted with Y"C[PO(OH)$_2$]$_2R^1$ in the presence of an activating reagent and a coupling additive if required. Y' is hereby advantageously an alcohol or amine function. Suitable activating reagents are, by way of example, EDC, DCC, DCI, PyClop, HBTU, HATU, HOSu, TBTU, T3P, BopCl and 3-Cl-1-pyridinium iodide. The substances HOBT, HOAt and HONB known to persons skilled in the art are usable, by way of example, as coupling additives. It is known to persons skilled in the art that these reactions are appropriately carried out with the addition of a base such as DIPEA. Persons skilled in the art are furthermore aware of different solvents to be used in the methods mentioned. They are able to independently produce these combinations of activating reagents, coupling additives, bases and solvents using their conventional knowledge and standard literature.

In an advantageous embodiment, Y"C[PO(OH)$_2$]$_2R^1$ is an amino functionalised bisphosphonate, such as pamidronate or alendronate and their protected derivatives. X—C[$(CH_2)_n$—Y']$_3$ or Pg-X—C[$(CH_2)_n$—Y']$_3$ are reacted with Y"C[PO(OH)$_2$]$_2R^1$ in the presence of a means of reduction. Y' is hereby an aldehyde or a ketone. Suitable means of reduction are, by way of example, $NaBH_4$, $NaBH_3CN$, NaBH(OAc)$_3$, as well as $H_2$ and metal catalysts. Persons skilled in the art know different solvents to be used in the methods mentioned. They are able to independently produce these combinations of means of reduction and solvents using their conventional knowledge and standard literature.

In another advantageous embodiment, Y"C[PO(OH)$_2$]$_2R^1$ is an amino or alcohol functionalised bisphosphonate, such as pamidronate or alendronate and their protected derivatives. X—C[$(CH_2)_n$—Y']$_3$ or Prot-X—C[$(CH_2)_n$—Y']$_3$ with a suitable leaving group Y' is reacted with Y"C[PO(OH)$_2$]$_2R^1$. Suitable leaving groups are, by way of example, —OTs, OMs, —OTf and halides. Persons skilled in the art know different solvents to be used in the methods mentioned. They are able to independently produce these combinations of leaving groups and solvents using their conventional knowledge and standard literature.

In an advantageous embodiment, Y"C[PO(OH)$_2$]$_2$R$^1$ is an amino functionalised bisphosphonate, such as pamidronate or alendronate and their protected derivatives. X—C[(CH$_2$)$_n$—Y]$_3$ or Pg-X—C[(CH$_2$)$_n$—Y]$_3$ is reacted with Y"C[PO(OH)$_2$]$_2$R$^1$. Y' is hereby an isothiocyanate or an isocyanate. Persons skilled in the art know different solvents to be used in the methods mentioned. They are able to independently produce these combinations of means of reduction and solvents using their conventional knowledge and standard literature.

In another advantageous embodiment, Y"C[PO(OH)$_2$]$_2$R$^1$ is a carbonyl functionalised bisphosphonate or a protected derivative thereof. X—C[(CH$_2$)$_n$—Y]$_3$ or Pg-X—C[(CH$_2$)$_n$—Y]$_3$ is reacted with Y"C[PO(OH)$_2$]$_2$R$^1$. Y' is hereby an O-alkylhydroxylamine or the corresponding hydrohalide. Persons skilled in the art know different solvents to be used in the methods mentioned.

In another advantageous embodiment, Y"C[PO(OH)$_2$]$_2$R$^1$ is an azide functionalised bisphosphonate or a protected derivative thereof. X—C[(CH$_2$)$_n$—Y]$_3$ or Pg-X—C[(CH$_2$)$_n$—Y]$_3$ is reacted with Y"C[PO(OH)$_2$]$_2$R$^1$ in the presence of a copper catalyst. Y' is hereby an alkyne. Persons skilled in the art know different solvents and copper catalysts to be used in the methods mentioned. They are able to independently produce these combinations of catalysts and solvents using their conventional knowledge and standard literature.

In another advantageous embodiment, Y"C[PO(OH)$_2$]$_2$R$^1$ is an alkyne functionalised bisphosphonate or a protected derivative thereof. X—C[(CH$_2$)$_n$—Y]$_3$ or Pg-X—C[(CH$_2$)$_n$—Y]$_3$ is reacted with Y"C[PO(OH)$_2$]$_2$R$^1$ in the presence of a copper catalyst. Y' is hereby an azide. Persons skilled in the art know different solvents and copper catalysts to be used in the methods mentioned. They are able to independently produce these combinations of catalysts and solvents using their conventional knowledge and standard literature.

If a protective group Pg has been introduced, this protective group is optionally removed at the end, i.e. after the formation of Pg-X-Ad{(CH$_2$)$_n$—Y—C[PO(OH)$_2$]$_2$R$^1$}$_3$, and the deprotected product is subsequently purified.

The compounds according to formula (I) according to the present invention are suitable to be used in a method to functionalise surfaces. The functionalisation hereby occurs via dip and rinse by dipping the surfaces to be functionalised into a solution of the compounds according to the present invention.

The compounds according to the present invention are advantageously dissolved in an aqueous buffer solution which comprises a salt concentration significantly higher than physiological salt concentrations (0.9 wt.-% of NaCl). MOPS (3(N-morpholine)-propane sulfonic acid) is, by way of example, a suitable buffer. NaCl and K$_2$SO$_4$ and mixtures thereof are suitable salts. The salt concentration advantageously amounts to between 10 and 20 wt.-% and the buffer concentration to between 0.05 and 0.2 mmol.

The X group of the compounds according to the present invention is suitable to be optionally coupled to an effector. The coupling of X to the effector is hereby suitable to be carried out both in solution, i.e. before the functionalisation of the surface, as well as on the surface, i.e. after the functionalisation of the surface. Effectors are, by way of example, ether groups, ester groups, heteroaromatic compounds, dyes, metal complexes, polymers (for example polyethylene glycols), pharmaceutical active agents (for example antibiotics, bisphosphonates), biomolecules (for example an amino acid), peptides, carbohydrates and terpenes. If the effector is a polymer and if this is a polyethylene glycol, it is advantageously a group —(O—CH2-CH$_2$)q-R$^3$ oder —(CH2-CH2-O)q-R$^3$, wherein q is a number between 1 and 10 and R$^3$ is defined as described under formula 1.

In an advantageous embodiment, the coupling of X is carried out by means of click chemistry. "Click reactions" are understood by persons skilled in the art to be energetically favoured reactions which run specifically and result in a single product. These are efficient reactions which are suitable to be carried out very easily. Click reactions are used in molecular biology, the development of active agents, biotechnology, macromolecular chemistry and material sciences. The concept of the click reaction was established by K. Barry Sharpless and describes reactions which

- are structured in a modular manner,
- comprise a wide scope of application,
- are suitable to be carried out with high yields,
- occur stereospecifically,
- allow for simple reaction conditions (as non-sensitive as possible against water and oxygen),
- occur in environmentally-friendly solvents and/or solvents which are easily removable, such as water, or occur in a solvent-free manner,
- require simple purification (extraction, phase separation, distillation or crystalisation) or no purification at all.

"Click reactions" are, in general, strongly thermodynamically favoured. This is frequently more than 84 kJ/mol, which results in a fast reaction with high selectivity for a single product. These are frequently carbon-heteroatom bond formations.

Chemical reactions which fulfill these criteria are:

- the carbonyl chemistry of the "non-aldol type", such as the formation of urea, thiourea, oximes, imines, aromatic heterocycles and hydrazones, and the formation of carbamides and amides,
- cyclo additions to unsaturated C—C bonds, in particular 1,3-dipolar cyclo additions such as the Huisgen cycloaddition, and also Diels-Alder reactions,
- nucleophilic substitutions, in particular the ring opening of strained, electrophilic heterocycles such as aziridines and epoxides,
- addition reactions at C—C multiple bonds, mostly in an oxidative manner such as, by way of example epoxidation, aziridination or dihydroxylation, but also Michael additions of Nu-H, wherein Nu is a nucleophile.

In another advantageous embodiment, the coupling of the effector to the X group occurs via conventional substitution or addition reactions which do not belong to the abovementioned conditions of a click reaction. These conventional reactions comprise, by way of example, the formation of ether, the esterification of a carboxylic acid or the formation of amide.

Particularly advantageously, the surfaces to be functionalised are metallic surfaces comprising iron and/or titanium or surfaces comprising apatite and/or glass. It is known to persons skilled in the art that bones of vertebrates comprise approximately 50% apatite, approximately 70% dentine and more than 95% tooth enamel. Modern dental prostheses, such as dental fillings and implants, frequently comprise apatite and/or devices which comprise iron and/or titanium. It is furthermore known that the surfaces of endosprostheses, for example for hip and knee joints, comprise iron and/or titanium. The compounds according to the present invention according to formula (I) as well as the compounds which are suitable to be obtained from them and coupled to an effector, are therefore suitable for the surface functionalisation of dental and joint endosprostheses.

PRACTICAL EMBODIMENTS

Practical Embodiment 1

Synthesis scheme

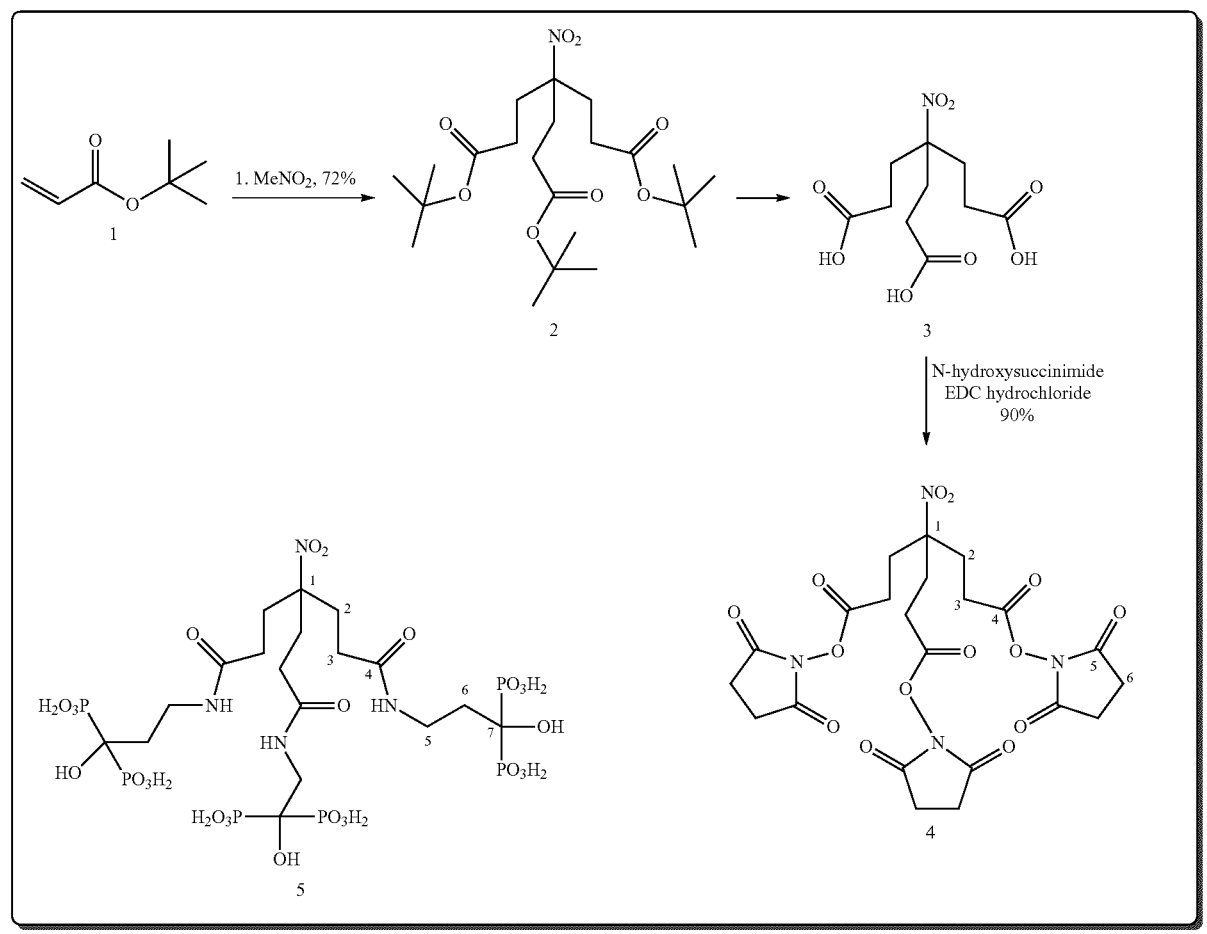

a) Production of the NHS Ester 4

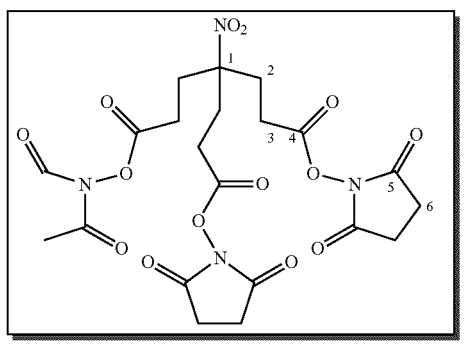

$C_{22}H_{24}N_4O_{14}$
M = 568,4 g/mol

The tricarboxylic acid 3 (0.19 g, 0.68 mmol) was dissolved in dioxane (30 mL). Subsequently, N-hydroxysuccinimide (NHS) (0.35 g, 3.0 mmol) was added, followed by EDC hydrochloride (0.48 g, 3.0 mmol). The reaction solution was stirred for 24 h at room temperature. Subsequently, the dioxane was removed in the vacuum. The residue obtained was taken up in EtOAc, washed three times with $H_2O$ and dried over $Na_2SO_4$, and the EtOAc was removed in the vacuum.

The NHS ester 4 (0.35 g, 0.61 mmol, 90%) was obtained as colourless solid.

MS (ESI): m/z (%)=591.1 (100) [M+Na$^+$].

b) Bisphosphonate Coupling 5

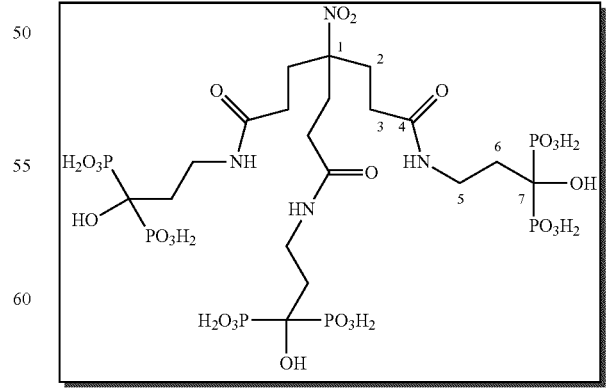

$C_{19}H_{42}N_4O_{26}P_6$
M = 928,4 g/mol

The NHS ester (0.35 g, 0.62 mmol) was dissolved in $H_2O$ (30 mL), and pamidronate (0.52 g, 2.23 mmol) and $Et_3N$ (1.7 mL, 12.4 mmol) were added. The reaction solution was stirred for 24 h at room temperature. Subsequently, the $H_2O$ was removed in the vacuum. The product obtained was purified by means of HPLC.

The invention claimed is:

1. A compound according to formula (I)

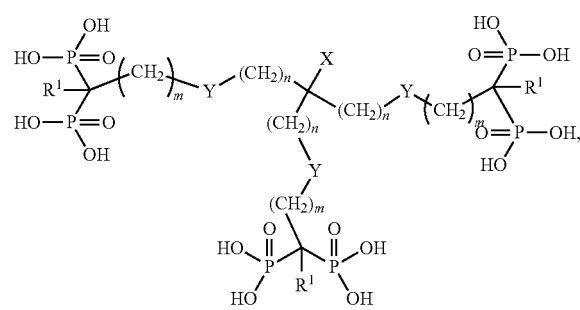

(I)

wherein n and m each, independently, is an integer between 0 and 10, $R^1$ is a hydrogen atom or a hydroxy group, Y is a bond, —$CH_2$—, —CH=CH—, —C≡C—, —O—, —S—, —S—S—, —NH—, —O—NH—, —NH—O—, —HC=N—O—, —O—N=CH—, —$NR^2$—, -aryl-, -heteroaryl-, —(C=O)—, —O—(C=O)—, —(C=O)—O—, —NH—, —(C=O)—, —(C=O)—NH—, —$NR^2$—(C=O)—, —(C=O)—$NR^2$—, —NH—(C=O)—NH—, or —NH—(C=S)—NH—, $R^2$ is a linear alkyl group with 1 to 10 C atoms or a branched or cyclic alkyl group with 3 to 10 C atoms, X is —$(CH_2)_p$—$R^3$; a branched alkyl, alkenyl or alkynyl group with 3 to 10 C atoms; a cyclic alkyl, alkenyl or alkynyl group with 3 to 10 C atoms; or an aryl or heteroaryl group, p is an integer between 0 and 10

$R^3$ is —$NH_2$, —$NO_2$, —OH, —SH, —O—$NH_2$, —NH—$NH_2$, —N=C=S—, —N=C=O, —CH=$CH_2$, —C≡CH, —COOH, —(C=O)H, or —(C=O)$R^4$ wherein the hydroxy, thio, amino or C=O groups are optionally protected by a protective group, —$N_3$, —$OR^4$, —$COOR^4$, —$NR^4R^5$, —CO—$NHR^4$, —$CONR^4R^5$, —NH—CO—$R^4$, or 4-(2,5-dioxopyrrol-1-yl), and $R^4$ and $R^5$ each, independently, is a linear alkyl group with 1 to 10 C atoms, a linear alkenyl or alkynyl group with 2 to 10 C atoms, a branched alkyl, alkenyl or alkynyl group with 3 to 10 C atoms, or a cyclic alkyl or alkenyl group with 3 to 10 C atoms, wherein, if X is a branched alkyl, alkenyl and alkynyl group, a cyclic alkyl or alkenyl group, an aryl or heteroaryl group, then one C atom of this group X is optionally substituted with $R^3$.

2. The compound according to claim 1, wherein Y is a bond, —$CH_2$—, —NH—(C=O)—, —(C=O)—NH—, or —NR'.

3. The compound according to claim 1, wherein n is an integer between 0 and 3.

4. The compound according to claim 1, wherein m is an integer between 0 and 3.

5. The compound according to claim 1, wherein X is —$(CH_2)_p$—$R^3$, and p is an integer between 0 and 3.

6. The compound according to claim 1, wherein

X is —$(CH_2)_p$—$R^3$, $R^3$ is —OH, —$NH_2$, —$NO_2$, —NH—$NH_2$, —$NR^4R^5$, —O—$NH_2$, —NH—(C=O)—C≡CH, —C≡CH, —N=C=S, —N=C=O, —COON, —(C=O)H, or —(C=O)$R^4$, and p is an integer between 0 and 3.

* * * * *

UNITED STATES PATENT AND TRADEMARK OFFICE
CERTIFICATE OF CORRECTION

Page 1 of 1

PATENT NO.        : 8,829,233 B2
APPLICATION NO.   : 13/821321
DATED             : September 9, 2014
INVENTOR(S)       : Wolfgang Maison et al.

It is certified that error appears in the above-identified patent and that said Letters Patent is hereby corrected as shown below:

<u>Title page:</u>

Item (75), "Mucke" should be -- Mücke --.

<u>In the Claims:</u>

At Column 11, line 29, "–C=C–," should be -- –C≡C–, --.

Signed and Sealed this
Twentieth Day of October, 2015

Michelle K. Lee
*Director of the United States Patent and Trademark Office*